United States Patent [19]

Blakemore

[11] 4,385,119
[45] May 24, 1983

[54] MAGNETIC BACTERIA AND PRODUCTS DERIVED THEREFROM

[75] Inventor: Richard P. Blakemore, Durham, N.H.

[73] Assignee: BioMagnetech Corp., New York, N.Y.

[21] Appl. No.: 134,438

[22] Filed: Mar. 27, 1980

[51] Int. Cl.$^3$ ............................ C12P 3/00; C12R 1/01; C12N 13/00; C12N 1/00
[52] U.S. Cl. ................................. 435/168; 435/173; 435/820; 435/822; 435/253
[58] Field of Search ............... 435/168, 170, 173, 803, 435/820, 822, 253

[56] References Cited

U.S. PATENT DOCUMENTS 3,597,318  8/1971  Sutherland et al. ............ 435/803 X

OTHER PUBLICATIONS

Metzler, *Biochemistry-The Chemical Reactions of Living Cells*, Academic Press, Inc., New York, 119 (1977).
Balkwill et al., *J. of Bacter.*, 141(3), 1399-1408 (Mar. 1980).
Butler, et al., *Journal of Geophysical Research*, 80(29), 4049-4058, (1975).
Jacobs et al., *The Physical Review*, 100(4), 1060-1067 (1955).
Wolin et al., *J. Biol. Chem.*, 238(8), 2882-2886 (1963).
Blakemore, *Science*, 190, 377-379 (1975).
Blakemore et al., *J. of Bacter.*, 140(2), 720-729 (Nov. 1979).
Frankel et al., *Science*, 203, 1355-1356, (Mar. 30, 1979).
Maratea, Characterization of a Magnetotactic Spirillum, Strain MS-1, A Thesis, U. of N.H., Dec. 1979.
Woods Hole Notes, 8, 3 (1976).
Frankel et al., *Journal of Magnetism and Magnetic Materials*, 15-18, 1562-1564 (1980).
Blakemore, *Abs. Annu. Meet. Am. Soc. of Micro.*, p. 185 (1979).
Blakemore et al., Proc. 18th Annu. Life Sci. Symp., 400 (1979), Phillips et al. editors.
Kalmijn et al., *Animal Migration, Navigation and Homing*, Springer-Verlag, New York, 344 (1978).
Denham et al., *IEEE Transactions on Magnetics*, 16(5), 1006-1007 (1980).
Blakemore et al., *Nature*, 286, 384-385 (1980).

*Primary Examiner*—Esther M. Kepplinger
*Attorney, Agent, or Firm*—Cooper, Dunham, Clark, Griffin & Moran

[57] ABSTRACT

A biologically pure culture of a bacterium of the genus Aquaspirillum, designated MS-1, has been found to contain chains (so-called magnetosomes) of single domain magnetite particles. The magnetite particles are roughly cubic and are about 500 Å on a side and each of the chains contains approximately 290 magnetite particles. These magnetite particles can be recovered from the bacterium and usefully employed in magnetic recording devices and the like.

19 Claims, 4 Drawing Figures

MAGNETIC BACTERIA AND PRODUCTS DERIVED THEREFROM

The invention described herein was made in the course of grants or awards from the National Science Foundation and the Office of Naval Research.

BACKGROUND OF THE INVENTION

This invention relates to a biologically pure strain of magnetotactic bacteria and to products derived therefrom.

Magnetotactic bacteria were first reported by Blakemore in *Science*, 190, 377 (1975). Several species of these bacteria, extracted from both fresh water and marine environments, were observed to orient and to swim in a preferred direction relative to the geomagnetic field. Magnetotactic bacteria from the Northern Hemisphere were observed to orient and swim towards the North, while it was predicted (and later confirmed) that magnetotactic bacteria from the Southern Hemisphere would orient and swim towards the South. Reversal of the ambient magnetic field, e.g., by Helmholz coils, caused the cells to reverse directions within one second. Killed cells also oriented in uniform fields as low as 0.1 G. In this and other respects, the cells behaved like single magnetic domains in a ferromagnetic material.

The magnetotactic behavior of the bacteria was attributed to cellular iron localized in crystal-like particles, 1000 to 1500 Å long within the bacteria. As reported above, the bacteria contained these iron-rich particles arranged in chains. Each cell had one or two of these chains, consisting of five to ten particles apiece. Clumps of the particles were also observed outside of the cells. It was speculated that the iron-containing particles equip the bacteria with a permanent ferromagnetic dipole moment.

SUMMARY OF THE INVENTION

Definitive studies of the chemical nature of the iron in magnetotactic bacteria has not been possible up to now because the organisms have not been available in pure culture. By means of the present invention, a biologically pure culture of a new strain of bacteria, designated MS-1 is isolated and cultured on a special growth medium rich in iron and products are derived therefrom. MS-1 is a magnetotactic Aquaspirillum. A non-magnetic variant of the strain may be cultured from MS-1 with a growth medium lacking iron and provided with abundant $O_2$. The iron-rich particles in MS-1 were found to be comprised of the mineral magnetite, $Fe_3O_4$. Frankel, Blakemore and Wolfe, *Science*, 203, 1355 (1979).

Magnetite may be extracted from the magnetotactic cells in the form of a coated chain of single domain particles. These particles are roughly cubic, about 500 Å on a side. Each chain contains about 20 particles. The chain of magnetite particles together with their bounding layers or envelopes have been termed "magnetosomes". The magnetosomes are unusual structures which find many useful applications, such as on magnetic recording tape.

DETAILED DESCRIPTION OF THE INVENTION

Figure 1:
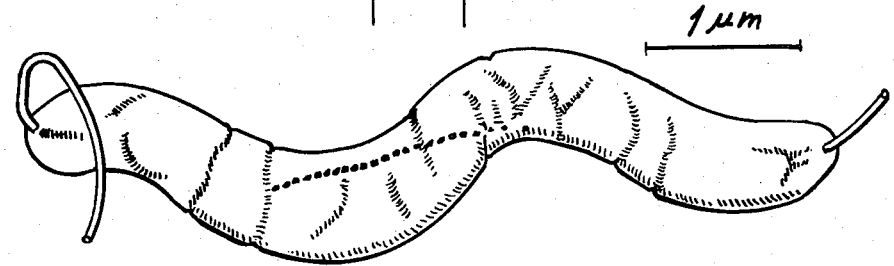
FIG. 1 is an illustration of an isolated cell of strain MS-1 showing the magnetite particles.
Figure 2:
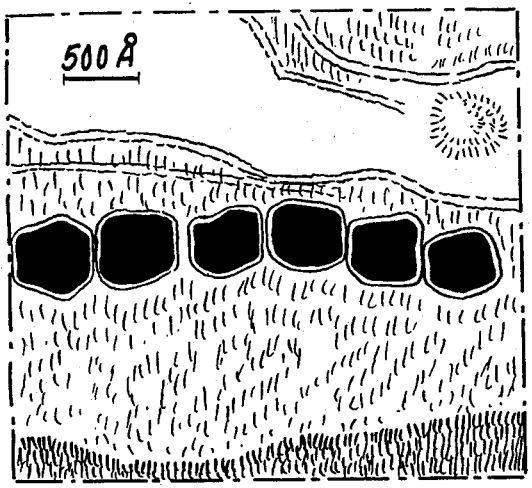
FIG. 2 is an illustration of the magnetite particles of MS-1 under higher magnification.

A magnetotactic bacterium was isolated from fresh water swamps and was cultured in the laboratory on a special growth medium. Frankel, Blakemore and Wolfe, *Science*, 203, 1355 (1979). The organism is a magnetotactic Aquaspirillum and appears to be a new bacterial species by criteria separate from its magnetic properties. It has been designated strain MS-1. A culture of this microorganism has been deposited in the permanent collection of the American Type Culture Collection, Rockville, Md. A subculture of the microorganism may be obtained upon request. Its accession number in this repository is ATCC 31632.

Isolation and Growth of Strain MS-1

Inocula for isolating magnetic bacteria were initially obtained from enriched bog water by application of magnetic fields. Blakemore, Maratea and Wolfe, *J. Bact.*, 140, 720 (1979). Permanent bar magnets were used to separate large numbers of motile magnetic cells from sediment. These magnetotactic cells (of at least six distinct morphological types) were washed in filtered, sterilized bog water and injected through the stoppers of culture tubes containing prereduced, semisolid isolation medium. The isolation medium consisted of (per 90 ml of distilled water): 10 ml of filtered swamp or bog water; 1 ml of vitamin elixir and 1 ml of mineral elixir [Wolin, Wolin and Wolfe, *J. Biol. Chem.*, 238, 2882 (1963)]; and 0.5 mM potassium phosphate buffer (pH 6.7). To this mixture were added: 5 μg of vitamin B-12, 25 mg of $NH_4Cl$; 10 mg of sodium acetate (anhydrous); 0.2 mg of resazurin; and 90 mg of Ionagar No. 2 (Oxoid). The pH was adjusted to 6.7 with NaOH. This medium was prereduced under nitrogen, using titanium citrate as the reducing agent, and was subsequently dispensed into culture tubes in an anaerobic hood. Inoculated tubes were incubated at 22° C. in the dark until growth became evident. A well-isolated area of growth was homogenized, and cells were cloned by serial dilution into tubes containing molten, prereduced isolation medium containing 0.85% (wt/vol) Ionagar No. 2. Well-isolated colonies which appeared in these tubes after 1 week at 30° C. were homogeneous as evidenced by microcopy. However, cells were again cloned, and the process was repeated a third time before cultures were considered pure.

Strain MS-1 was maintained at 30° C. with weekly transfers in screw-capped culture tubes containing a semisolid growth medium consisting of (per 98 ml of distilled water): 1 ml of vitamin elixir; 1 ml of mineral elixir; 5 mM of $KH_2PO_4$; 25 μM ferric quinate; and 0.2 mg of resazurin. To this mixture were added (per 100 ml): 0.1 g of succinic acid; 20 mg of sodium acetate (anhydrous); 10 mg of $NaNO_3$; 5 mg of sodium thioglycolate; and 130 mg of agar (GIBCO Laboratories). The ferric quinate solution was prepared by combining 2.7 g of $FeCl_3$ and 1.9 g of quinic acid with 1 liter of distilled water. Before adding the agar, the pH of the medium was adjusted to 6.7 with NaOH. The medium was boiled, and 12 ml was added to each screw-capped tube (16 by 125 mm) containing approximately 0.1 ml of 5% (wt/vol) sodium thioglycolate in distilled water. Tubes of semisolid growth medium were autoclaved with caps tightened and allowed to stand overnight for the establishment of $O_2$ gradients. Inocula consisted of 0.2 ml (ca. $7 \times 10^7$ cells) per 12 ml of medium. Chemically defined growth medium was identical to the semisolid growth medium, except that agar was omitted and the medium was sealed under a gas atmosphere of known composition as described below.

A homogeneous population of nonmagnetic cells was obtained from cultures of MS-1 grown in isolation medium made with distilled water rather than bog water. Cells grown in this medium, especially with twice as much as the usual amount of nitrate and succinate, grew nonmagnetically. To obtain a non-magnetic culture from the strain MS-1 for comparative studies, cells grown for five successive transfers in this medium were cloned three successive times. Stocks of this nonmagnetic variant of stain MS-1 were subsequently maintained in defined growth medium without ferric quinate.

Cells of stain MS-1 in the magnetic and nonmagnetic state were mass cultured in chemically defined growth medium and this medium minus ferric quinate, respectively. Agar was omitted from media for mass cultures. Glass bottles (150 ml to 1 liter) were filled to approximately one-third of their volume with medium. The atmosphere of each was replaced with $N_2$, and it was then crimp-sealed with a serum stopper or closed with a rubber stopper wired in placed before autoclaving. Cells were inoculated into cooled medium by injection through the stopper. Sufficient air was added to each bottle at the time of inoculation to provide 0.6 to 1.0% (vol/vol) $O_2$ in the gas phase for routine culture. Growth of magnetic cells was inhibited when the initial $O_2$ concentration was above about 6%. However, non-magnetic cells grew at these higher $O_2$ concentrations.

A glass carboy was sealed with a rubber stopper fitted with a bottomless, screw-capped, 16-mm tube which served as a gas outlet and port for inoculation and sampling. A 12-g stainless needle which had been inserted through the stopper was used as a gas inlet. It was attached to a 40-cm length of tubing contained within the carboy to allow incurrent gas to sparge through the culture medium. The medium in each carboy was autoclaved under air. Hot medium was sparged with sterile $N_2$ while being cooled at 30° C. It was then inoculated and incubated at 30° C. after sealing the carboy against further gas exchange. Midway through growth, when the culture became reduced as evidenced by a color change, its pH was adjusted to 6.7 aseptically with 0.5 M succinic acid, and it was continuously aerated with sterile air by means of an aquarium pump.

A variety of organic compounds in addition to succinic acid can be used as carbon and energy sources in the growth medium. Those which support growth of MS-1 are intermediates of the tricarboxylic acid cycle, as well as $\beta$-hydroxybutyric, tartaric, lactic, and pyruvic acids. Nitrogen or nitrates are desirable ingredients of the growth medium. In some cases, the cells did not grow without the nitrate, and in other cases cell growth was markedly improved with the addition of nitrates.

Vitamins are not required for growth or magnetotactic behavior of the organism but do prevent the cells from acquiring a swollen appearance. Ferric quinate is not required for cell growth but without it, the cells are not magnetotactic. Neither ferric chloride, ferric citrate, nor iron chelated by L-DOPA, protocatechuic acid, L-epinephrine, L-arterenol, or EDTA satisfied the requirement for $Fe_3O_4$ synthesis by MS-1.

Structure of Magnetic Bacteria and Isolated Magnetic Components

Magnetotactic cells of strain MS-1 possess a right-handed helical morphology. Each cell has single bipolar flagella (FIG. 1). The cell envelope of stain MS-1 appears in thin sections to consist of two distinct layers, a lipopolysaccharide (LPS) or "wall membrane" and a cytoplasmic membrane. The wall member is trilaminate in cross-section. Two types of inclusion bodies are present within the cytoplasm, (i) those with a structure resembling poly-$\beta$-hydroxybutyrate (PHB) granules and (ii) iron-rich particles, described in detail below.

Magnetotactic cells of strain MS-1 contain $2.0 \pm 0.2\%$ (wt/vol) of their dry weight in iron. Non-magnetotactic cells of strain MS-1 lack the iron-rich particles of the magnetic cells. Magnetic cells contain 10 times more iron than non-magnetic cells on a dry weight basis. However, the disparity is even greater than the dry weight figures because of the large weight contribution of iron. In all respects aside from the magnetic properties and the presence of the iron particles, the magnetic and non-magnetic cells of strain MS-1 are similar.

Electron microscopy confirms that magnetotactic cells and coccoid bodies of spirillum strain MS-1 contains intracellular chains of electron-dense, iron-rich particles similar to those observed previously in other magnetotactic bacteria. These particle chains, which are not known to occur in other spirilla, do not resemble any of the various known types of inclusion bodies in non-magnetotactic bacterial cells. They are novel bacterial cell components, the ultrastructure of which has not yet been thoroughly studied.

Figure 3:
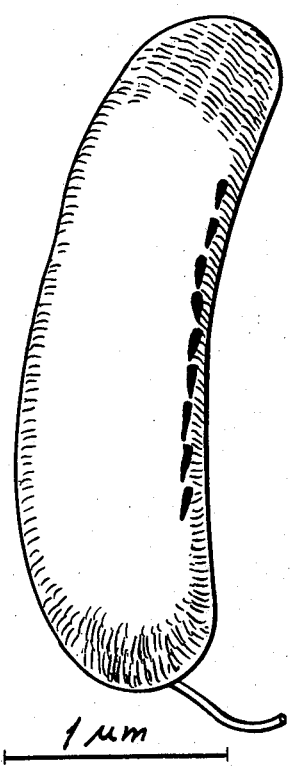
FIG. 3 is an illustration of a magnetotactic bacterium having pyramidal-shaped magnetic particles.
Figure 4:
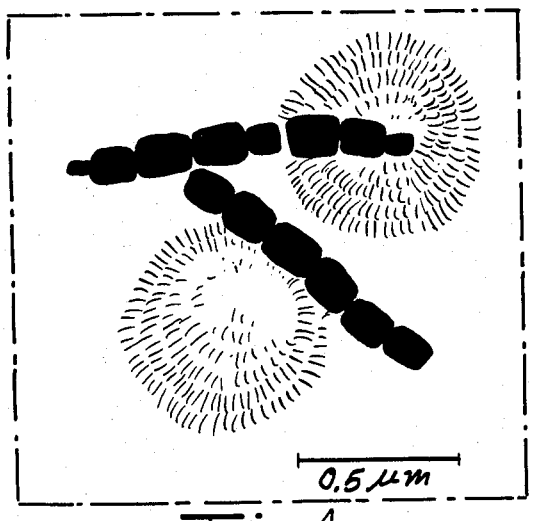
FIG. 4 is an illustration of parallelpiped-shaped magnetic particles in a magnetic bacterium.

High resolution scanning electron microscopy of the iron-rich particles shows that most of them are roughly cubic with rounded corners, although some of them may be described as octahedral. Thus, the particles are similar to those found in other magnetotactic bacteria (FIG. 4), with the exception of some varieties found in the Southern Hemisphere, which have iron-rich particles of pyramidal or arrowhead shape (FIG. 3).

The size of the particles in MS-1 varied from about 250 to 550 Å in width, the average length of a side being about 420 to 500 Å. Energy dispersive X-ray measurements show that the particles in strain MS-1 have high iron content. Mossbauer spectroscopy of $^{57}Fe$ conclusively shows that the iron in the particles is magnetite, $Fe_3O_4$, with possibly minor admixture of $\gamma$-$Fe_2O_3$ and another iron-containing compound similar to ferritin. *Science*, 203, 1355 (1979). Non-magnetotactic cells lack the magnetite crystals. Thus, magnetotaxis in MS-1 is associated with intracellular magnetite. The presence of intracellular magnetite is evidence of a process of bacterial synthesis from the soluble (chelated) iron contained in the growth medium.

When viewed in negatively-strained preparation of whole cells, the electron-dense particles are arranged in a single chain that runs the length of the cell in a generally straight line. The number of particles in each chain varies from about 5 to about 50, averaging about 20 particles per chain. The largest particles are located in the center of the chain, while those at the ends are often smaller. While magnetic forces may help to hold the particles together in chains, it seems likely that they are also connected structurally. This has been confirmed by electron microscopy which shows that the particles are enveloped by membranes.

When viewed in thin-sectioned preparations, each particle is surrounded by an inner electron-transparent layer 16 Å thick and by an outer electron-dense layer 14 Å thick. Adjacent particles in a chain are sometimes in direct contact with each other, but usually are separated by a distance of 30–190 Å. The space between the particles does not appear to contain distinct structures though cytoplasmic material appears to be present there.

The layers surrounding the particles are still uncharacterized. The electron-dense layer could be a protein "membrane" similar to those observed surrounding other types of bacterial inclusion bodies. However, the protein "membrane" of other inclusion bodies is not separated from the body by an electron-light layer. It is possible that the electron-dense layer is a true biological membrane (e.g., a lipid bilayer) rather than a protein structure. It is also conceivable that the membrane is actually trilaminate but that the inner-most layer, being electron-dense, cannot be distinguished from the particle itself. Additional studies are needed to ascertain the tube chemical nature of the layers.

The chains appear to be a stable structural characteristic of the particles. The particles remain arrayed in chains in degenerate cell forms termed coccoid bodies which develop under adverse conditions. The chains may be extracted from the cells of MS-1 by a variety of methods. For example, they may be extracted by mechanical means, such as sonication, or by chemical disruption or lysis of the cells with sodium dodecyl sulfate. The chains may then be purified by treatment with sodium dodecyl sulfate and then collected by centrifugation or with a magnet after being extracted from the cells.

In view of their unique structure and chemical nature, as well as their role in bacterial magnetotaxis, the chains of particles together with their bounding layers have been termed "magnetosomes". The magnetosomes exhibit magnetic remanence, orient in externally applied magnetic fields, and have an X-ray diffraction spectrum characteristic of magnetite. Since they, or structures similar to them, have been reported in all magnetotactic bacteria described to date, but have not been observed in any non-magnetotactic cells, there can be little doubt that they are directly responsible for the alignment of magnetic cells in magnetic fields. This is also supported by theoretical calculations.

The magnetic properties of magnetite particles depend on their size and shape. For a particle of roughly cubic shape with side dimension d, there is a range of d over which the particle will be a single magnetic domain. Butler and Banerjee, *J. Geophys. Res.*, 80, 4049, (1973), calculated that at 300° K., magnetite particles will be single domain if d is within the range of 500 to 700 Å. Thus, with d=500 Å, the magnetite particles in strain MS-1 are within the single domain size range.

The magnetic properties of a chain of single domain particles have been considered by Jacobs and Bean, *Phys. Rev.*, 100, 1060 (1955). Their results showed that because of strong interparticle interactions, the preferred orientation of the individual particles is such that their axes of magnetization are parallel, north-to-south along the chain direction. Thus, the entire chain acts as a single magnetic dipole with a moment equal to the sum of the particle moments. They also calculated the applied field necessary to cause reversal of the chain magnetization, postulating a fanning mechanism for individual moment reversal. This mechanism requires an applied field of several hundred gauss to induce reversal in a chain of magnetite particles, in qualitative agreement with experimental results obtained using magnetic bacteria. Kalmijn and Blakemore in *Animal Migration, Navigation and Homing*, K. Schmidt-Koenig and W. T. Keeton, Eds. (Springer Verlag, N.Y., 1978), p. 344.

The magnetic moment per bacterium, M, can be calculated using the known magnetic moment per unit volume of magnetite, $M_v=480$ emu/cc. For a single particle of volume $1.25 \times 10^{-16}$ cc, the magnetic moment $m=6.1 \times 10^{-14}$ emu. For a cell containing an average chain length of twenty two particles, the total moment per bacterium $M=1.3 \times 10^{-12}$ emu. In the geomagnetic field of 0.5 G, the total magnetic energy of a cell $MH=6.6 \times 10^{-13}$ erg. This value is over an order of magnitude greater than thermal energy, $kT$ ($4.1 \times 10^{-14}$ erg at 300° K.).

The orientation of a bacterium or equivalently, the orientation of an ensemble of bacteria in the earth's magnetic field of 0.5 G in water at ambient temperatures can be calculated from the well-known Langevin theory of classical paramagnetism. The calculations show that each bacterium contains a sufficient but not an excessive amount of single domain sized magnetite in an appropriate configuration to produce orientation in the earth's magnetic field at ambient temperature, i.e., the cell's chain of magnetite crystals functions as a biomagnetic compass.

The simplest hypothesis for the mechanism of magnetotaxis is passive orientation of the bacterium resulting from the torque exerted by the ambient magnetic field on its biomagnetic compass as it swims. An estimate of the rotation time for a bacterium in water can be obtained from the rotational diffusion equation. Calculations of this nature show that the time required to reorient 180° in response to a sign reversal of a 0.5 G magnetic field is about 0.4 sec. This result is of the order of reversal times measured by Kalmijn and Blakemore for bacteria taken from mud samples.

Since most magnetotactic bacteria from the Northern Hemisphere are observed to swim northward and hence downward, the compass in these cells must have a fixed orientation with respect to the flagellum, with the north seeking pole opposite to the flagellum. Analogously, bacteria from the Southern Hemisphere have the south seeking pole opposite the flagellum. Blakemore, Frankel and Kalmijn, submitted for publication in *Nature*, 1980. This orientation could be preserved in cell division if the compass is partitioned between two daughter cells. Subsequently, during the magnetite biosynthesis the magnetic moments of nascent magnetite particles at the ends of the pre-existing chains would become oriented along the chain direction by interaction with the chain dipole moment.

Both strain MS-1 and its inclusion bodies may have useful applications. For example, the magnetosomes or the single domain magnetite crystals may find use in connection with magnetic recording tape or in connection with medical application. Other uses will undoubtedly be found for both the bacterium and its inclusion bodies.

While the invention has been described by reference to specific examples, these references are for purposes of illustration only, and should not be construed to limit the spirit or scope of the invention.

We claim:

1. A process for producing a single domain magnetite structure, comprising growing a biologically pure culture of a microorganism designated strain MS-1, said microorganism being a magnetotactic Aquaspirillum, said microorganism having the identifying characteristics of ATCC 31632, and extracting said structure from said microorganism.

2. A process for producing a single domain magnetite structure according to claim 1 wherein the structure is extracted from the microorganism by mechanical means.

3. A process according to claim 2 wherein the structure is extracted by sonication.

4. A process for producing a chain of magnetic structures together with an enveloping membrane, comprising growing a biologically pure culture of a microorganism designated strain MS-1, said microorganism being a magnetotactic Aquaspirillum, said microorganism having the identifying characteristics of ATCC 31632, and extracting a chain of magnetic structures together with an enveloping membrane from said microorganism.

5. A process for producing a chain of magnetic structures together with an enveloping membrane according to claim 4 wherein the chain is extracted from the microorganism by mechanical means.

6. A process according to claim 5 wherein the chain is extracted by sonication.

7. A magnetic structure extracted from a biologically pure culture of a magnetic bacterium wherein the shape of the structure is substantially pyramidal.

8. A chain of magnetic structures together with an enveloping membrane extracted from a magnetic bacterium wherein the shape of the magnetic structures is substantially pyramidal.

9. A chain of magnetic structures together with an enveloping membrane extracted from a magnetic bacterium wherein the magnetic structures are parallelpiped-shaped.

10. A process for producing a chain of magnetic structures together with an enveloping membrane comprising growing a biologically pure culture of magnetic bacteria and extracting a chain of magnetic structures together with an enveloping membrane from said magnetic bacteria.

11. A process for producing a chain of magnetic structures together with an enveloping organic membrane according to claim 10 wherein the chain is extracted from the bacteria by mechanical means.

12. A process according to claim 11 wherein the chain is extracted by sonication of the bacteria.

13. A substantially pyramidal-shaped magnetite structure having a long dimension in the range of about 250 to about 550 Å.

14. A magnetic structure extracted from a biologically pure culture of a magnetic spirillum wherein the structure is substantially pyramidal-shaped.

15. A chain of magnetic structures together with an enveloping membrane extracted from a magnetic spirillum wherein the magnetic structures are pyramidal-shaped.

16. A chain of magnetic structures together with an enveloping membrane extracted from a magnetic spirillum wherein the magnetic structures are parallelpiped-shaped.

17. A process for producing a chain of magnetic structures together with an enveloping membrane comprising growing a biologically pure culture of magnetic spirilla and extracting a chain of magnetic structures together with an enveloping membrane from said magnetic spirilla.

18. A process for producing a chain of magnetic structures together with an enveloping membrane according to claim 17 wherein the chain is extracted from the magnetic spirilla by mechanical means.

19. A process according to claim 18 wherein the chain is extracted by sonication.

* * * * *